United States Patent [19]
Greenwald et al.

[11] Patent Number: 5,880,131
[45] Date of Patent: *Mar. 9, 1999

[54] HIGH MOLECULAR WEIGHT POLYMER-BASED PRODRUGS

[75] Inventors: Richard B. Greenwald, Somerset; Annapurna Pendri, Matawan, both of N.J.

[73] Assignee: Enzon, Inc., Piscataway, N.J.

[ * ] Notice: The term of this patent shall not extend beyond the expiration date of Pat. No. 5,840,900.

[21] Appl. No.: 537,207

[22] Filed: Sep. 29, 1995

Related U.S. Application Data

[63] Continuation-in-part of Ser. No. 380,873, Jan. 30, 1995, Pat. No. 5,614,549, which is a continuation-in-part of Ser. No. 140,346, Oct. 20, 1993, abandoned.

[51] Int. Cl.⁶ ......... A61K 31/44; A61K 31/335; C07D 491/22; C07D 305/14
[52] U.S. Cl. ......... 514/279; 514/283; 514/449; 546/48; 546/51; 549/510; 549/511
[58] Field of Search ......... 546/48, 51; 514/279, 514/283, 449; 549/510, 511

[56] References Cited

U.S. PATENT DOCUMENTS

| | | | |
|---|---|---|---|
| 4,101,380 | 7/1978 | Rubinstein et al. | 195/63 |
| 4,179,337 | 12/1979 | Davis et al. | 435/181 |
| 4,275,000 | 6/1981 | Ross | 260/112 R |
| 4,534,899 | 8/1985 | Sears | 260/403 |
| 4,582,805 | 4/1986 | Bozzelli et al. | 435/180 |
| 4,680,338 | 7/1987 | Sundoro | 525/54.1 |
| 4,814,470 | 3/1989 | Colin et al. | 514/449 |
| 4,904,582 | 2/1990 | Tullis | 435/6 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | |
| 5,059,699 | 10/1991 | Kingston et al. | 549/511 |
| 5,091,176 | 2/1992 | Braatz et al. | 424/78.17 |
| 5,122,614 | 6/1992 | Zalipsky | 548/520 |
| 5,136,060 | 8/1992 | Holton | 549/510 |
| 5,157,049 | 10/1992 | Haugwitz et al. | 514/449 |
| 5,227,400 | 7/1993 | Holton et al. | 514/444 |
| 5,229,526 | 7/1993 | Holton | 549/213 |
| 5,489,589 | 2/1996 | Wittman et al. | 514/232.8 |
| 5,498,729 | 3/1996 | Domb | 548/500 |

FOREIGN PATENT DOCUMENTS

| | | |
|---|---|---|
| 0510356 | 3/1992 | European Pat. Off. . |
| 0524093 | 7/1992 | European Pat. Off. . |
| 0437563B1 | 2/1995 | European Pat. Off. ....... A61K 47/48 |
| WO 81/01145 | 4/1981 | WIPO . |
| 91/02763 | 3/1991 | WIPO . |
| WO 95/10304 | 4/1995 | WIPO . |

OTHER PUBLICATIONS

Bioconjugate Chemistry Sep./Oct. 1992 vol. 3, No. 5; 351–362, Maeda, Hiroshi et al.
Journal of Bioactive and Compatible Polymers vol. 10 Jan. 1995, 51–66; Ohya, Yuichi et al.
Polymer Bulliten 18, 487–493 (1987) Gehrardt et al.
J. of Controlled Release 10, (1989) 145–154 Veronese, F et al.
Cancer Chemother Pharmacol (1992) 31 255–257 Waud, W. et al.
Biotechnology and Applied Biochemistry 9, 258–268 (1987) Buckn, A. et al.
"Novel, Water–Soluble Phosphate Derivatives of 2'–Ethoxycarbonyl Paclitaxel . . . ", Bioorganic & Medicinal Chemistry Letters, vol. 5, No. 3, pp. 247–252 (1995).
"Synthesis and Antitumor Evaluation of 2'–Oxycarbonyl Paclitaxel" Bioorganic & Medicinal Chemistry Letters, vol. 4, No. 15, pp. 1861–1864 (1994).
Bonina, F.P. et al., "In vitro and in vivo evaluation of polyoxyethylene indomethacin esters as dermal prodrugs", Journal of Controlled Release 34 (1995) 223–232.
Devineni, D. et al., "Preparation and in Vitro Evaluation of Magnetic Microspere–Methotrexate Conjugate Drug Delivery Systems", Bioconjugate Chem. 6 (1995) 203–210.
Nichifor, M. et al., "Macromolecular Prodrugs of 5–Fluorouracil. 1: Synthesis and Hydrolytic Stability", Journal of Bioactive and Compatible Polymers, vol. 10 (Jul. 1995) 199–222.
Senter, P.D. et al., "Poly(ethylene glycol)–Doxorubicin Conjugates Containing β–Lactamase–Sensitive Linkers" Bioconjugate Chem. 6 (1995) 389–394.
Duncan, R. And F. Spreafico, "Polymer Conjugates: Pharmacokinetic Considerations for Design and Development" Clin. Pharmacokinet 27(4) (1994), 290–306.
Duncan, R., "Drug–polymer conjugates: potential for improved chemotherapy" Anti–Cancer Drugs 3 (1992) 175–210.

(List continued on next page.)

*Primary Examiner*—Ba K. Trinh
*Attorney, Agent, or Firm*—Roberts & Mercanti, LLP

[57] ABSTRACT

High molecular weight, water-soluble prodrugs of the formula:

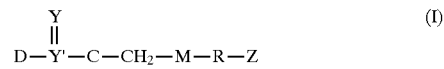

$$D-Y'-\overset{Y}{\underset{\|}{C}}-CH_2-M-R-Z \quad (I)$$

wherein:
D is a biologically active moiety;
M is X or Q;
X is an electron withdrawing group;
Q is a moiety containing a free electron pair positioned five or six atoms from Y';
Y and Y' are oxygen or sulfur;
R is a polyalkylene oxide; and
Z is OH, $C_{1-4}$ all moieties or

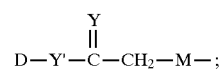

$$D-Y'-\overset{Y}{\underset{\|}{C}}-CH_2-M-;$$

are disclosed. In preferred embodiments, the prodrugs contain a polyethylene glycol having a molecular weight of at least about 20,000.

44 Claims, 7 Drawing Sheets

OTHER PUBLICATIONS

Maeda, H., "SMANCS and polymer–conjugated macromolecular drugs: advantages in cancer chemotherapy" Advanced Drug Delivery Reviews, 6(1991) 181–202.

Poiani, G.J., "Conjugates of cis–4–Hydroxy–L–proline and Poly(PEG–Lys), a Water Soluble Poly(ether urethane): Synthesis . . . in Vivo" Bioconjugate Chem. 5 (1994), 621–630.

Traber, M.G. et al., "Efficacy of water–soluble vitamin E in the treatment of vitamin E malabsorption in short–bowel syndrome" Am. J. Clin Nutr. 59 (1994), 1270–1274.

Nathan, A. et al., "Strategies for Covalent Attachment of Doxorubicin to Poly(PEG–Lys), a New Water–Soluble Poly(ether urethane)" Journal of Bioctive and Compatible Polymers, vol. 9, (1994), 239–251.

Inada, Y. et al., "Biomedical and biotechnological applications of PEG—and PM–modified proteins" Tibtech, 13 (1995), 86–91.

Weissleder, R., "Quantitation of Slow Drug Release from an Implantable and Degradable Gentamicin Conjugate In Vivo . . . Imaging" Antimicrobial Agents and Chemotherapy, 39 (1995), 839–845.

Ranucci, E. et al., "Pharmacokinetic results on naproxen prodrugs based on poly(ethyleneglycols)s", J. Biomater, Sci. Polymer Edn., 6 (1994), 141–147.

Commercon et al, Tetrahedron Letters, vol. 33, No. 36, pp. 5158–5188 (1992).

Magre et al, J. Org. Chem., vol. 51, pp. 797–802 (1986).

Gueritte–Voegelein et al, J. Med. Chem., 34, pp. 992–998 (1991).

Zalipsky et al, Eur. Polym. J., vol. 19, No. 12, pp. 1177–1183 (1983).

Ouchi et al, Drug Design & Discovery, vol. 9, pp. 93–105, (1992).

Mathew et al, J. Med. Chem., 35, pp. 145–151 (1992).

Cecchi et al, J. Med. Chem., vol. 24, pp. 622–625 (1981).

Weiner et al, Journal of Medicinal Chemistry, vol. 16, No. 5, (1973).

Nicolaou, Nature, vol. 364, pp. 464–466, 29 Jul. 1993.

Nathan et al, "Polymers Preprints", 31, 1990, pp. 213–214.

HIGH MOLECULAR WEIGHT POLYMER-BASED PRODRUGS

RELATED APPLICATIONS

This application is a continuation-in-part of U.S. patent application Ser. No. 08/380,873 filed Jan. 30, 1995, now U.S. Pat. No. 5,614,549 which, in turn, is a continuation-in-part of U.S. patent application Ser. No. 08/140,346 filed Oct. 20, 1993 now abandoned.

TECHNICAL FIELD

The present invention relates to water soluble prodrugs. In particular, the invention relates to the use of relatively high molecular weight non-antigenic polymers to prepare prodrugs.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal is either insoluble in aqueous fluids or is rapidly degraded in vivo. Alkaloids are often especially difficult to solubilize.

For example, several methods have been suggested to overcome the problems associated with administering paclitaxel, (also known as Taxol®, Bristol-Myers Squibb Co. NY, N.Y.), which is insoluble in water. Currently, taxol is administrated in physical admixture with a non-aqueous vehicle, cremophor-EL. This formulation, however, has several drawbacks. Hypersensitivity reactions have been associated with the vehicle and intravenous administration of the agent with this vehicle is also slow and causes discomfort to the patient.

Several methods have been suggested to enhance the aqueous solubility of taxol. See, for example, PCT WO 93/24476, U.S. Pat. No. 5,362,831, and Nicolaou, et al. *Angew. Chem. Int. Ed. Engl.* (1994) 33, No. 15/16, pages 1583–1587. Preparing water-soluble prodrug versions has also been explored.

Prodrugs include chemical derivatives of a biologically-active parent compound which, upon administration, will eventually liberate the active parent compound in vivo. Use of prodrugs allows the artisan to modify the onset and/or duration of action in vivo. In addition, the use of prodrugs can modify the transportation, distribution or solubility of a drug in the body. Furthermore, prodrugs may reduce the toxicity and/or otherwise overcome difficulties encountered when administering pharmaceutical preparations.

A typical example in the preparation of prodrugs can involve conversion of alcohols or thioalcohols to either organic phosphates or esters. *Remington's Pharmaceutical Sciences*, 16th Ed., A. Osol, Ed. (1980), the disclosure of which is incorporated by reference herein.

Prodrugs are often biologically inert or substantially inactive forms of the parent or active compound. The rate of release of the active drug is influenced by several factors including the rate of hydrolysis of the converted ester or other functionality.

Recently, polyethylene glycol and related polyalkylene oxides have been suggested as possible adjuncts for the preparation of taxol prodrugs. See PCT WO 93/24476 supra, for example. PEG has also been conjugated to proteins, peptides and enzymes to increase aqueous solubility and circulating life in vivo as well as reduce antigenicity. See, for example, U.S. Pat. Nos. 5,298,643 and 5,321,095, both to Greenwald, et al. These latter two references disclose, inter alia, biologically-active conjugates having substantially hydrolysis-resistant bonds (linkages) between a polyalkylene oxide and the target moiety. Thus, long-lasting conjugates rather than prodrugs per se were prepared. In most situations, the average molecular weight of the polymer included in the conjugate was preferably about 5,000 daltons.

PCT WO 93/24476 discloses using an ester linkage to covalently bind taxol to water-soluble polyethylene glycols and provide a prodrug. Applicants, however, have discovered that the ester linkages described therein provide $t_{1/2}$ for hydrolysis of greater than four days in aqueous environments. Thus, most of the conjugate is eliminated prior to hydrolysis being achieved in vivo. It would be preferable to provide an ester linkage which allows more rapid hydrolysis of the polymer-drug linkage in vivo so as to generate the parent drug compound more rapidly.

It has also been surprisingly found that when only one or two polymers of less than 10,000 molecular weight are conjugated to alkaloids and/or organic compounds, the resulting conjugates are rapidly eliminated in vivo. In fact, such conjugates are so rapidly cleared from the body that even if a hydrolysis-prone ester linkage is used, not enough of the parent molecule is regenerated in vivo to make the PAO-drug conjugate worthwhile as a prodrug.

Ohya, et al., *J. Bioactive and Compatible Polymers* Vol. 10 January, 1995, 51–66, disclose doxorubicin-PEG conjugates which are prepared by linking the two substituents via various linkages including esters. The molecular weight of the PEG used, however, is only about 5,000 at best. Thus, the true in vivo benefits would not be realized because the conjugates would be substantially excreted prior to sufficient hydrolysis of the linkage to generate the parent molecules.

Yamaoka, et al. *J. Pharmaceutical Sciences*, Vol. 83, No. 4, April 1994, pages 601–606, disclose that the half-life of unmodified PEG in circulation of mice after IV administration extended from 18 minutes to one day when molecular weight was increased from 6,000 to 190,000. Yamaoka, et al., however, failed to consider the effect of linking the polymer to a drug would have on the drug. Also, Yamaoka, et al. failed to consider that aqueous solutions of higher molecular weight polymers are quite viscous and difficult to dispense through the narrow-bore devices used to administer pharmaceutical preparations.

In summary, previous prodrugs based on conjugates of parent drug compounds with water soluble polymers have not been successful due to a combination of excessively slow hydrolysis of the polymer from the parent drug and excessively rapid clearance of the prodrug from the body.

SUMMARY OF THE INVENTION

The present invention addresses the shortcomings described above. In one aspect of the invention, compositions of formula (I) are provided:

wherein:
D is a biologically active moiety;
M is X or Q;
X is an electron withdrawing group;
Q is a moiety containing a free electron pair positioned five or six atoms from Y';

Y and Y' are independently O or S; and

R is a polyalkylene oxide.

In these aspects of the invention, the polyalkylene oxide, R, can be further substituted with a moiety Z, wherein:

Z is a polymer capping group such as a $C_{1-4}$ alkyl moiety, an additional biologically active moiety or

where D' can be the same as D or a different biologically active moiety.

In some preferred embodiments of the invention, compositions of formula (II) and (III) are provided:

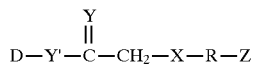

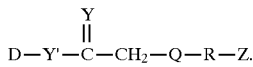

The prodrugs include a water-soluble polyalkylene oxide polymer (designated R herein). In particular, R is preferably a polyethylene glycol and has a molecular weight of at least about 20,000.

The prodrug compositions of the present invention can include one or more active compounds attached to the water-soluble polymer, each via a hydrolyzable linkage such as a suitably activated ester linkage. Thus, mono- and bis-polymer-based prodrugs are contemplated.

In certain preferred aspects of the invention, the active or parent compound (designated D herein) attached to the polymer is a taxane such as taxol or taxotere. In other aspects of the invention, the active or parent compound is camptothecin, etoposide or podophyllotoxin. In still further embodiments, non-oncolytic agents such as anti-inflammatory agents, including steroidal compounds, as well as therapeutic low molecular weight peptides such as insulin are also contemplated.

One of the chief advantages of the compounds of the present invention is that the prodrugs achieve a proper balance between the rate of linkage hydrolysis and the rate of clearance of prodrug from the body. The linkage between the polymer and the parent compound, also referred to herein as a biologically-active nucleophile, hydrolyzes at a rate which allows a sufficient amount of the parent molecule to be released in vivo before clearance of the prodrug from the plasma or body.

Methods of making and using the compositions described herein are also provided.

DETAILED DESCRIPTION OF THE INVENTION

A. THE PRODRUGS

Figure 1:
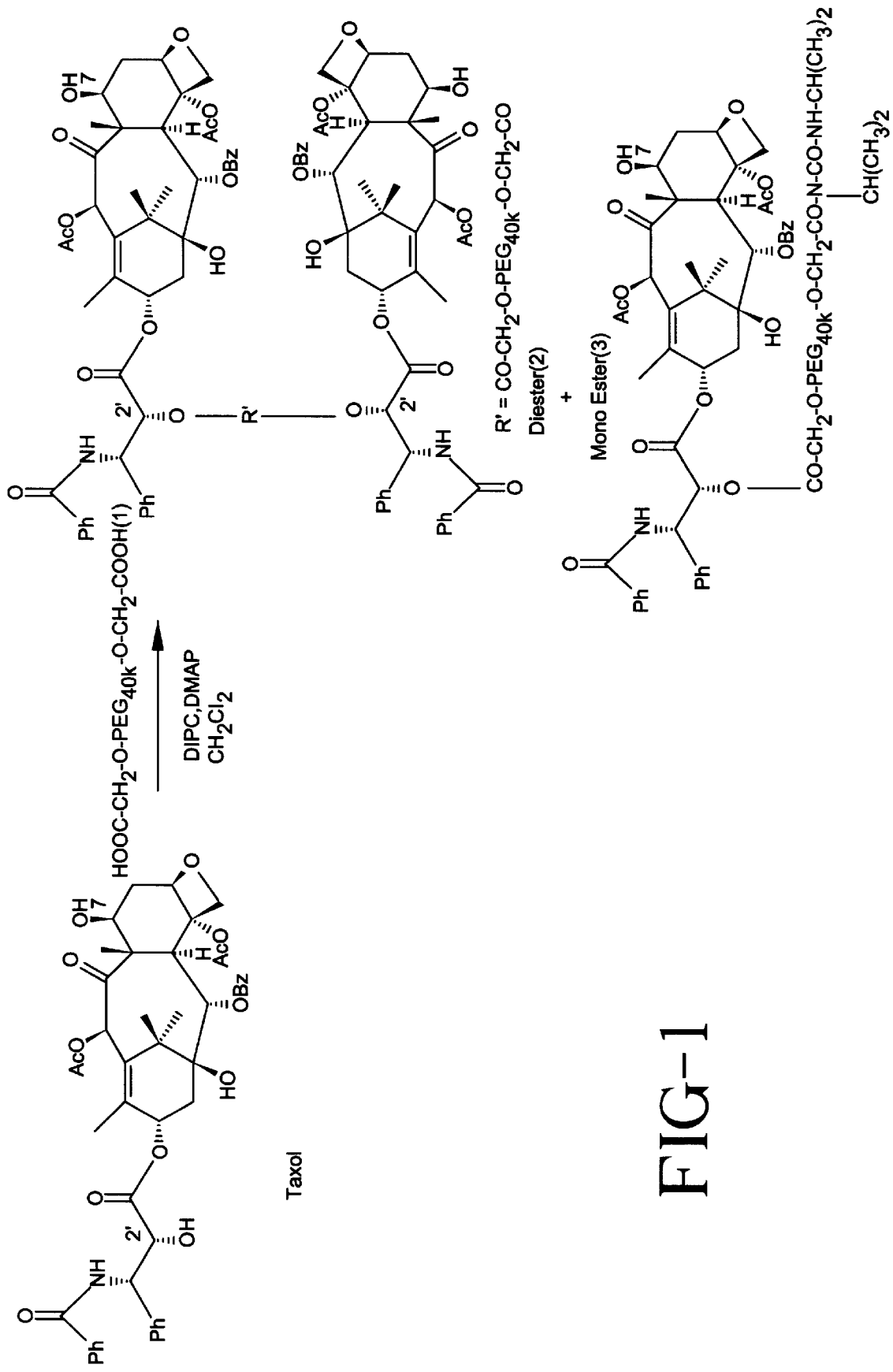
FIG. 1 is a schematic representation of the reactions carried out in accordance with Example 2.
Figure 2:
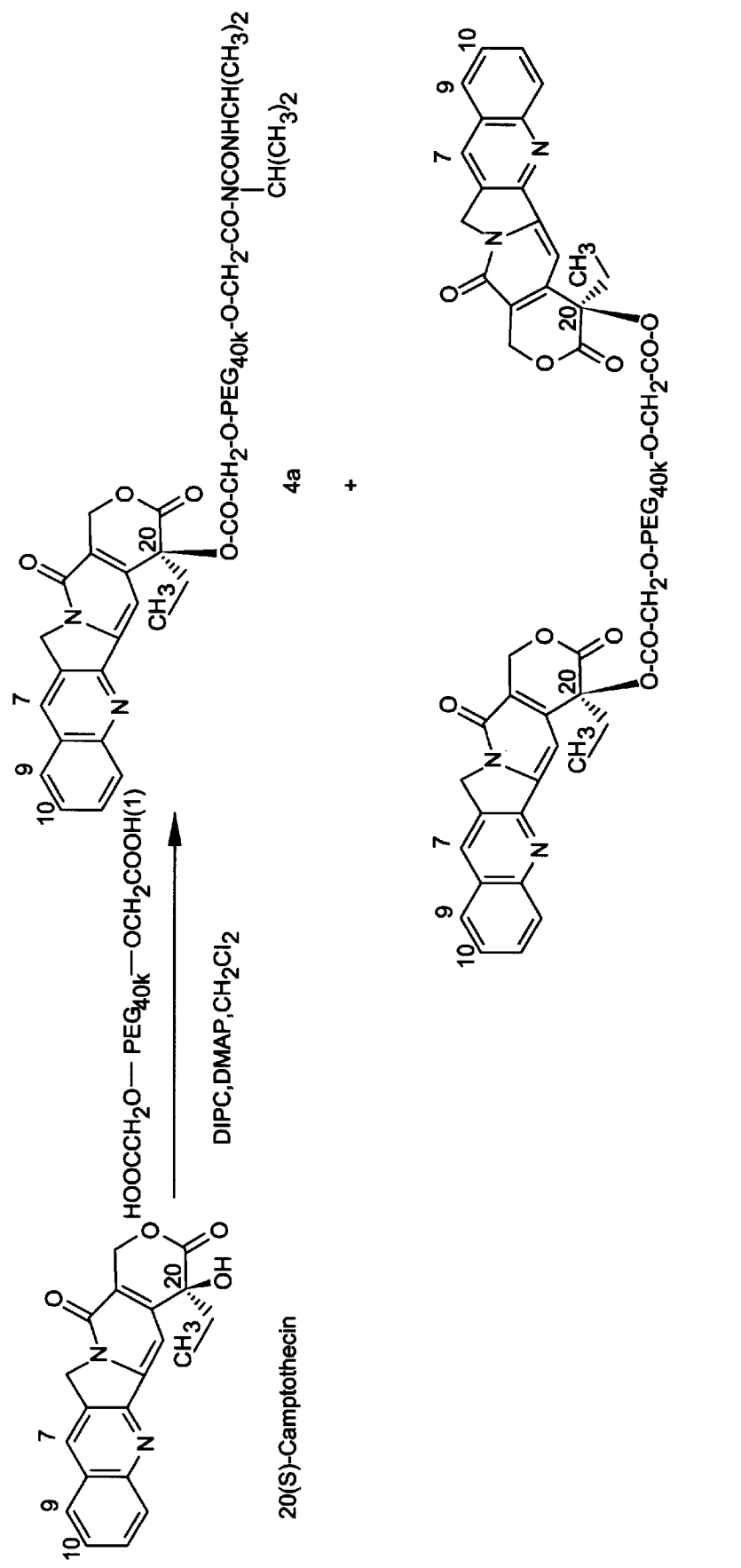
FIG. 2 is a schematic representation of the reactions carried out in accordance with Example 4.
Figure 3:
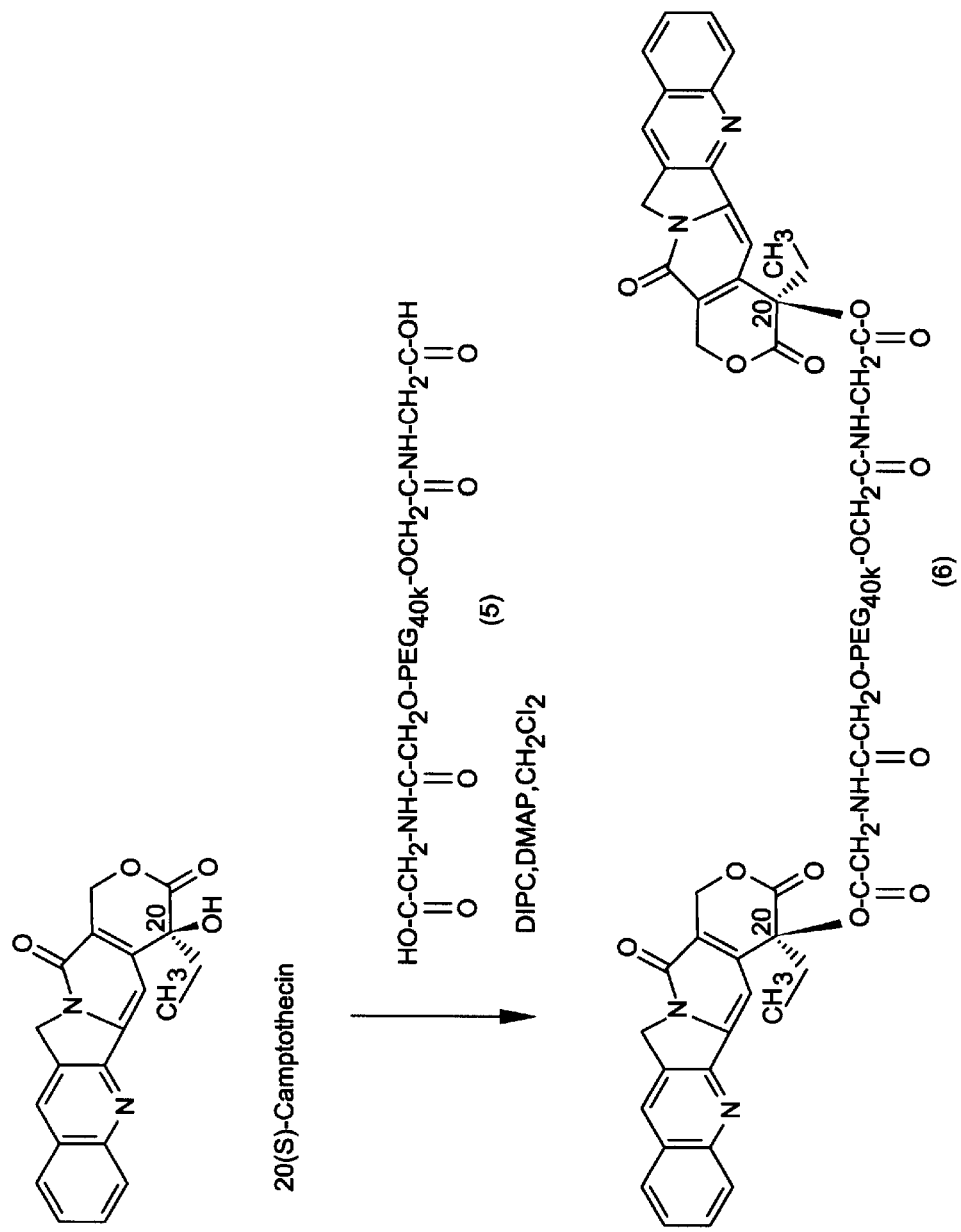
FIG. 3 is a schematic representation of the reactions carried out in accordance with Example 6.
Figure 4:
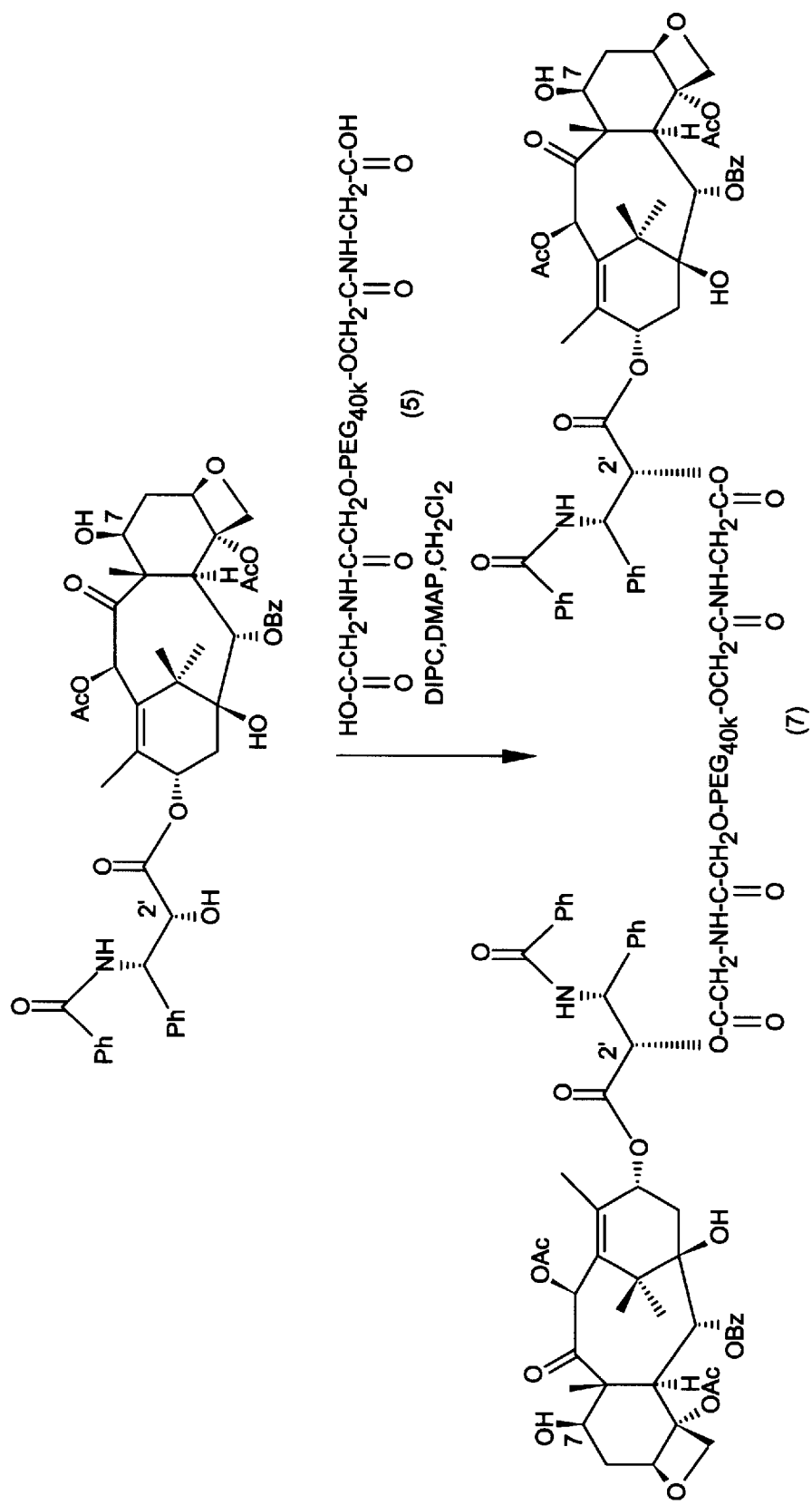
FIG. 4 is a schematic representation of the reactions carried out in accordance with Example 7.

The prodrug compositions of the present invention contain hydrolyzable linkages between the polymer portion and a biologically active moiety derived from a biologically active nucleophile, i.e. native or unmodified drug. These linkages are preferably ester linkages designed to hydrolyze at a rate which generates sufficient amounts of the biologically active parent compound in a suitable time. The term "sufficient amounts" for purposes of the present invention shall mean an amount which achieves a therapeutic effect.

In one aspect of the invention, the prodrugs of the invention are the formula (I), as set forth below:

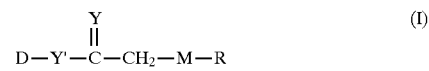

wherein:

D is a biologically active moiety;

M is X or Q;

X is an electron withdrawing group;

Q is a moiety containing a free electron pair positioned five or six atoms from Y';

Y and Y' are independently O or S;

R is a polyalkylene oxide.

Preferably, the polymer portion, designated R herein, is further substituted with a moiety Z selected from the group consisting of polymer capping groups, biologically active and inactive moieties, OH, $C_{1-4}$ alkyl moieties or

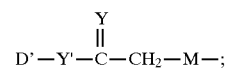

where D' is the same as D or a different biologically active moiety or even a capping group such as that set forth above.

Within Formula (I), Y and Y' are preferably oxygen.

In those aspects where M is X as shown below:

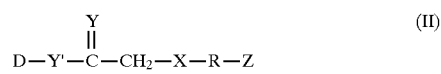

X is an electron withdrawing group which gives a substituted acetic acid with a pKa of less than about 4.0 upon hydrolysis of the prodrug ester. Thus, X can be one of O, OC(O)CH$_2$, —N(L)—C(O)—, —C(O)—N(L), C(O), N(L), S, SO or SO$_2$;

wherein L is selected from the group consisting of H, $C_{1-8}$ alkyls, cycloalkyls, aryls and aralkyls. Suitable alkyls include straight or branched alkyls, preferably methyl. Suitable aryls include phenyl or substituted phenyls; suitable aralkyls include benzyls. X is preferably one of O, —N(H)C(0)— or S or SO$_2$.

The moieties selected for X promote relatively rapid hydrolysis because of the low pKa of the resulting substituted acetic acid.

In another embodiment of the invention, compositions of Formula (III) are provided:

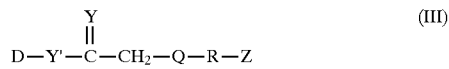

wherein:

D, Y', Y, R and Z are the same as that set forth above in Formula (I) and R is preferably attached to Q via a heteroatom, preferably O. Q is a moiety containing a free electron pair positioned three to six atoms from Y' as shown below in FIG. (IIIa)

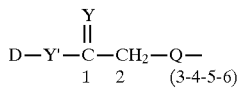
$$\begin{array}{cccc} & Y & & \\ & \parallel & & \\ D-Y'-C-CH_2-Q- & & \\ 1 & 2 & (3\text{-}4\text{-}5\text{-}6) & \end{array} \quad (IIIa)$$

In a preferred embodiment, the free electron pair is five atoms from Y'. Q can be selected from the non-limiting list of $C_{2-4}$ alkyls or cycloalkyls, aryls or aralkyl groups substituted with a member of the group consisting of OH, SH and NH(L), wherein L is a $C_{1-8}$ alkyl, cycloalkyl, aryl or aralkyl. The free electron pair can be anywhere along the Q moiety as long as the defined spacing between the free electron pair and Y' is maintained.

Some particularly preferred moieties for Q include:
—$CH_2$—C(O)—N(H)—, and ortho-substituted phenyl groups such as

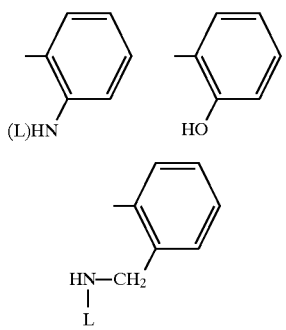

In these embodiments, the R—Z portion can be attached via L, a hetero atom (O,N,S) or an aryl group. Thus, Q, in formula (III), assists hydrolysis of the prodrug ester by anchimeric assistance because the free electron pair moiety can generate a three- to six-membered, but preferably five-membered, ring by-product upon hydrolysis of the ester.

In another alternative aspect of the invention, the methylene portion of Formula III is not included, as shown below in (IIIb):

$$\begin{array}{c} Y \\ \parallel \\ D-Y'-C-Q \end{array} \quad (IIIb)$$

In this aspect, it is understood that the defined spacing between the free electron pair and Y' is maintained.

In both Formulas (II) and (III), Z represents a terminal substitution of the water soluble polyalkylene oxide polymer. Suitable polymer terminal groups include hydroxyl, $CH_3$ or a $C_{1-4}$ alkyl when the prodrugs include a single biologically active moiety. On the other hand, the prodrugs of Formula (I) can also include disubstituted polymers. Thus, in the case of Formula (I), Z is a moiety of Formula (IV):

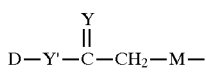
$$\begin{array}{c} Y \\ \parallel \\ D-Y'-C-CH_2-M- \end{array} \quad (IV)$$

wherein each of the variables is the same as that set forth for Formula (I) above.

In the particular case of Formula (II), Z is a moiety of Formula (V):

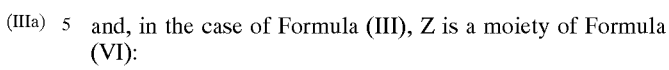
$$\begin{array}{c} Y \\ \parallel \\ D-Y'-C-CH_2-X- \end{array} \quad (V)$$

and, in the case of Formula (III), Z is a moiety of Formula (VI):

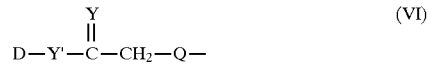
$$\begin{array}{c} Y \\ \parallel \\ D-Y'-C-CH_2-Q- \end{array} \quad (VI)$$

wherein each of the variables is the same as that set forth for Formula (II) above.

B. SUBSTANTIALLY NON-ANTIGENIC POLYMERS

The prodrug compositions of the present invention include a water-soluble polymer, R. Suitable examples of such polymers include polyalkylene oxides such as polyethylene glycols which are also preferably substantially non-antigenic.

In particular, polyethylene glycols (PEG's), mono-activated, $C_{1-4}$ alkyl-terminated PAO's such as monomethyl-terminated polyethylene glycols (mPEG's) are preferred when mono- substituted polymers are desired; bis-activated polyethylene oxides are preferred when disubstituted prodrugs are desired. In order to provide the desired hydrolyzable linkage, mono- or di-acid activated polymers such as PEG acids or PEG diacids are used. Suitable PAO acids can be synthesized by converting mPEG-OH to an ethyl ester. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester. See, for example, commonly assigned U.S. patent application Ser. No. 08/440,732 filed May 15, 1995. The disclosures of each of the foregoing are incorporated by reference herein.

Although PAO's and PEG's can vary substantially in molecular weight, polymers having molecular weight ranges of at least 20,000 are preferred. Polymers ranging from about 20,000 to about 80,000 are usually selected for the purposes of the present invention. Molecular weights of from about 25,000 to about 45,000 are preferred and 30,000 to about 42,000 are particularly preferred. The molecular weight of the polymer selected for inclusion in the prodrug must be sufficient so as to provide sufficient circulation of the prodrug during hydrolysis of the linker.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers maintained.

One type of preferred polymers useful in forming the prodrugs include polymers of the formula (VII)

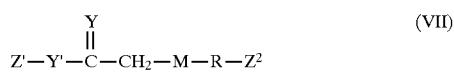
$$\begin{array}{c} Y \\ \parallel \\ Z'-Y'-C-CH_2-M-R-Z^2 \end{array} \quad (VII)$$

wherein:
M is X or Q;
Z' is OH or a $C_{1-4}$ alkyl;
$Z^2$ is OH, a $C_{1-4}$ alkyl or

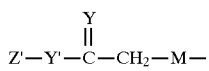

wherein each of M, Q, X, R, Y, and Y' are the same as that set forth above and at least one of Z' and $Z^2$ is OH.

Y and Y' are preferably O, and R has a molecular weight of about 20,000 or greater.

The following PEG acids and PEG diacids are especially preferred:

PEG—X—$CH_2$—COOH,

HOOC—$CH_2$—XPEG—X—$CH_2$—COOH,

and

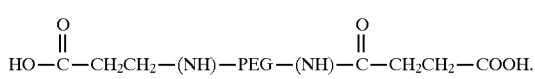

As an alternative to PAO-based polymers, effectively non-antigenic materials such as dextran, polyvinyl alcohols, carbohydrate-based polymers and the like can be used if the same type of ester activation is employed as described herein for PAO's such as PEG, i.e. conversion of alcohol to a 2-alkoxy acid. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

C. PRODRUG CANDIDATES

1. Taxanes and Taxane Derivatives

One class of compounds included in the prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs available from, for example, Signa Chemical of St. Louis, Mo. and/or Bristol Meyers Squibb are within the scope of the present invention. Representative taxanes are shown below.

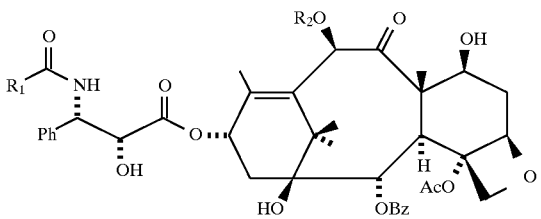

Taxol: $R_1 = C_6H_5$; $R_2 = CH_3CO$
Taxotere: $R_1 = (CH_3)_3CO$: $R_2 = H$

These compounds have been found to be effective anti-cancer agents. Numerous studies indicate that the agents have activity against several malignancies. To date, their use has been severely limited by, among other things, their short supply, poor water solubility and immunogenicity. One particularly beneficial class of taxanes are the 7-aryl-carbamates, represented below by Formula (VIII):

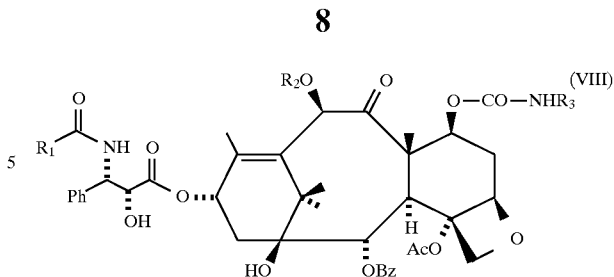

wherein, $R_1$ is $C_6H_5$ or $(CH_3)_3CO$;

$R_2$ is $CH_3CO$ or H;

$R_3$ is aryl, aralkyl, or heteroaryl.

Within this aspect, one particularly preferred taxane includes $R_3$ as phenyl.

Although the examples describe inter alia taxol for illustrative purposes, it is to be understood that the methods described herein are suitable for all taxanes and related molecules. The only limitation on this provision is that the selected taxanes must be capable of undergoing 2' position modifications described herein. Taxol, however, is a preferred taxane.

Formation of the taxane-based prodrugs of the invention is set forth below in section D and in the Examples.

Generally, a taxane having the 2' position available for substitution is reacted with a suitably activated polymer such as a PEG acid under conditions sufficient to cause the formation of a 2' ester linkage between the two substituents. As illustrative examples, taxol and taxotere are shown below:

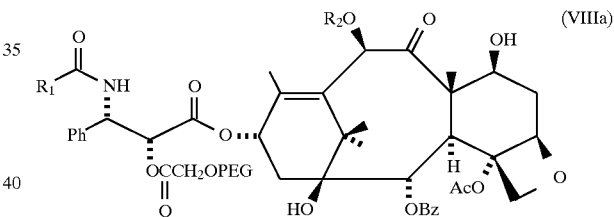

ProTaxol: $R_1 = C_6H_5$; $R_2 = CH_3CO$
ProTaxotere: $R_1 = (CH_3)_3CO$: $R_2 = H$ The corresponding diester can be prepared by reacting at least about 2 equivalents of taxane per polymer diacid. Even when two equivalents of taxane are reacted with the polymer diacid, the resulting conjugate can contain minor amounts (i.e. up to 25%) by weight of a monoester species containing an acyl urea distal to the polymer-taxane linkage with regard to the polymer. In these aspects of the invention, it is preferred that the polymer have a molecular weight of at least about 20,000.

2. Camptothecin and Related Topoisomerase I Inhibitors

Camptothecin is a water-insoluble cytotoxic alkaloid produced by camptoteca accuninata trees indigenous to China and nothapodytes foetida trees indigenous to India. Camptothecin and related compounds and analogs are also known to be potential anticancer or antitumor agents and have been shown to exhibit these activities in vitro and in vivo in laboratory animals. Camptothecin and related compounds are also candidates for conversion to the prodrugs of the present invention. See, for example, U.S. Pat. No. 5,004,758 and Hawkins, *Oncology*, Dec. 1992, pages 17–23. Camptothecin and related analogues have the structure:

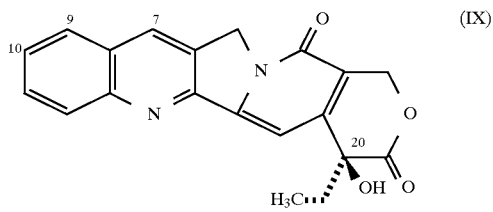

(IX)

20(S)-Camptothecin

| Camptothecin analogues | Position | | |
|---|---|---|---|
| | 7 | 9 | 10 |
| Topotecan | H | $CH_2N(CH_3)_2$ | OH |
| CPT-11 | $-CH_2-CH_3$ | H | 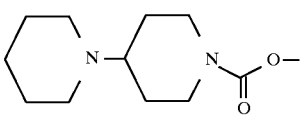 |

Formation of a monoester camptothecin prodrug can be accomplished by reacting one or more equivalents of a suitably activated polymer with one equivalent of the camptothecin derivative under conditions sufficient to effectively convert the 20-OH to an ester-linked polymeric based prodrug. Camptothecin diesters are similarly prepared by reacting at least about 2 and preferably greater equivalents of the camptothecin with a suitably prepared PAO diacid.

Figure 5:
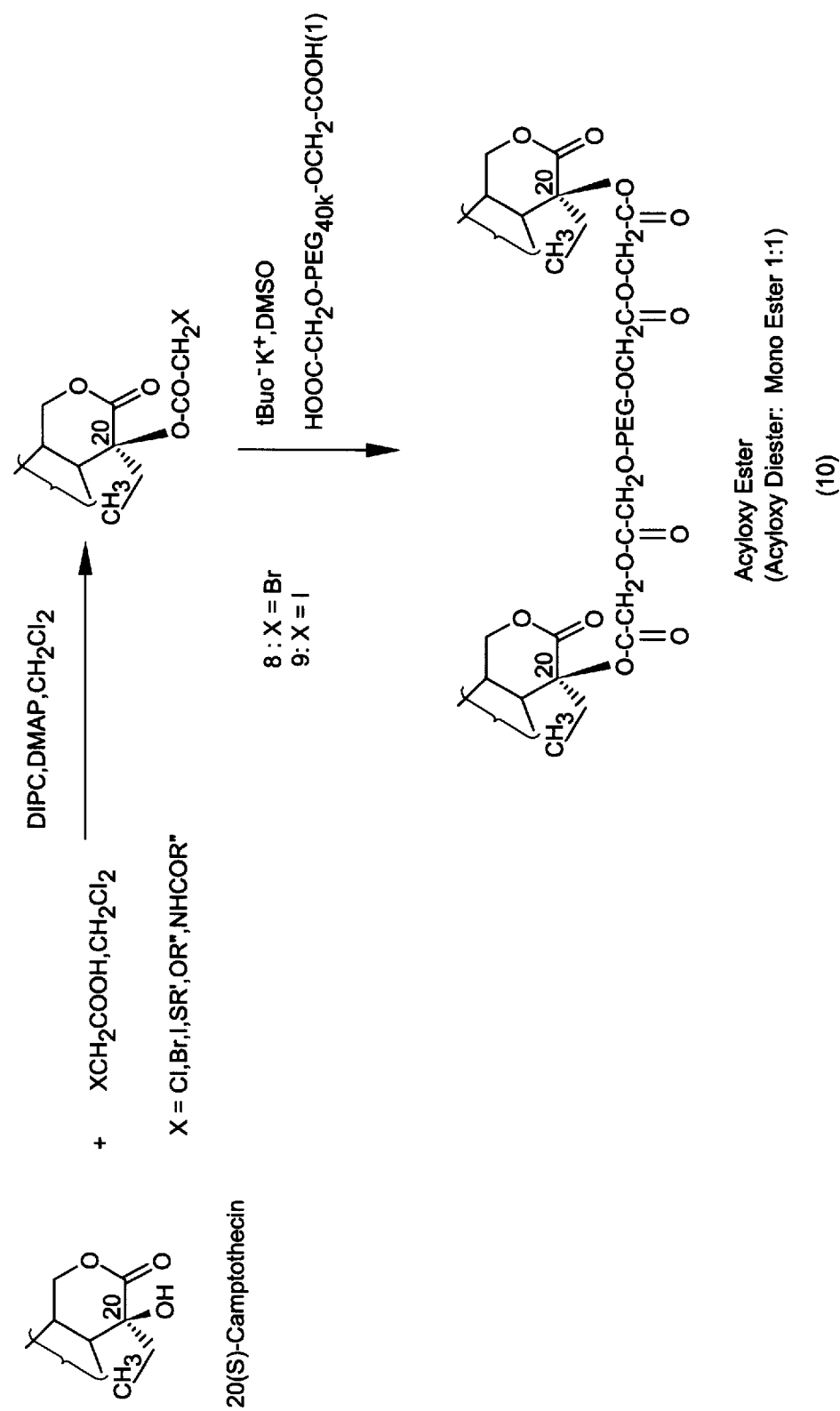
FIG. 5 is a schematic representation of the reactions carried out in accordance with Examples 8, 9 and 10.
Figure 6:
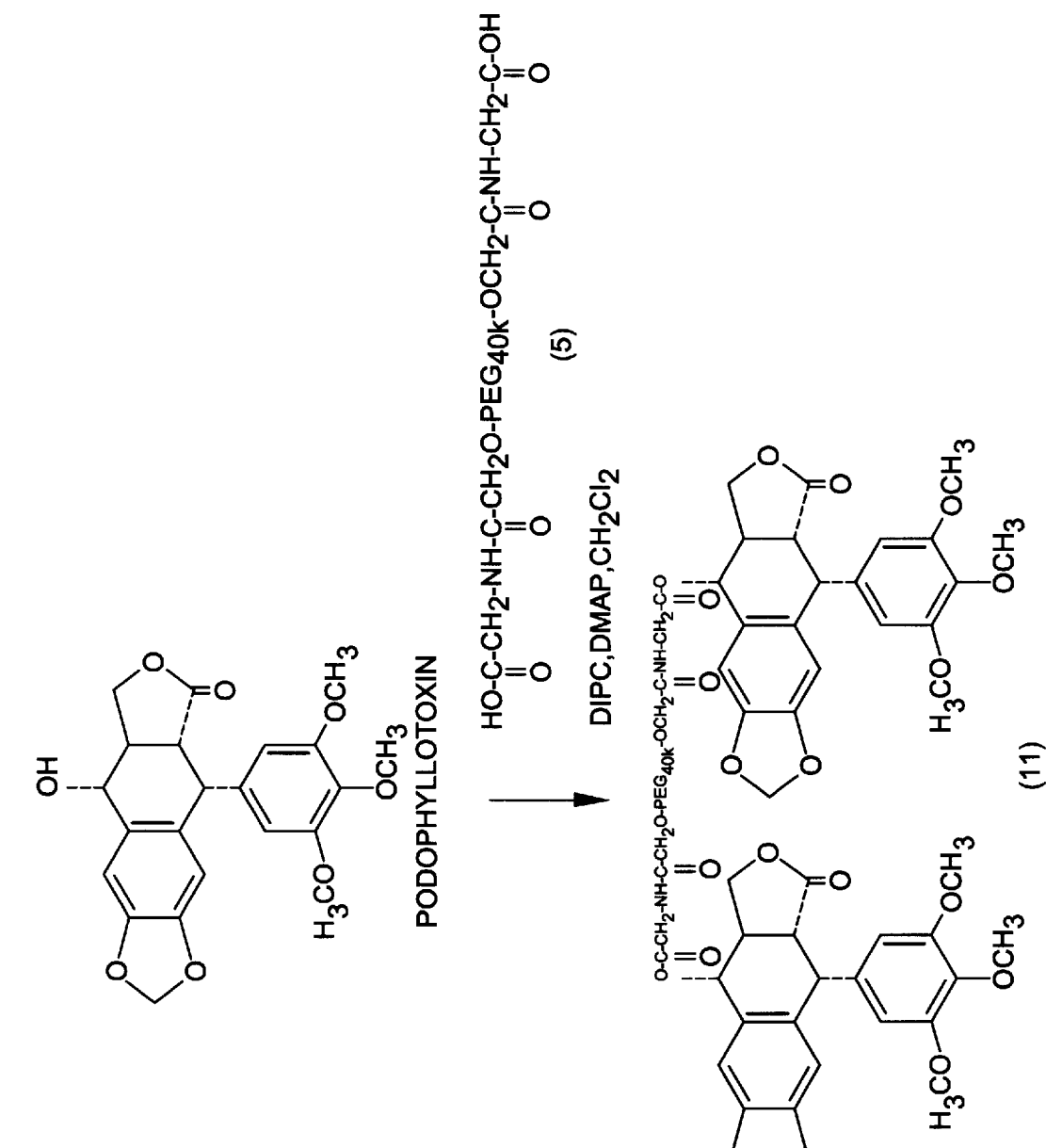
FIG. 6 is a schematic representation of the reactions carried out in accordance with Example 11.
Figure 7:
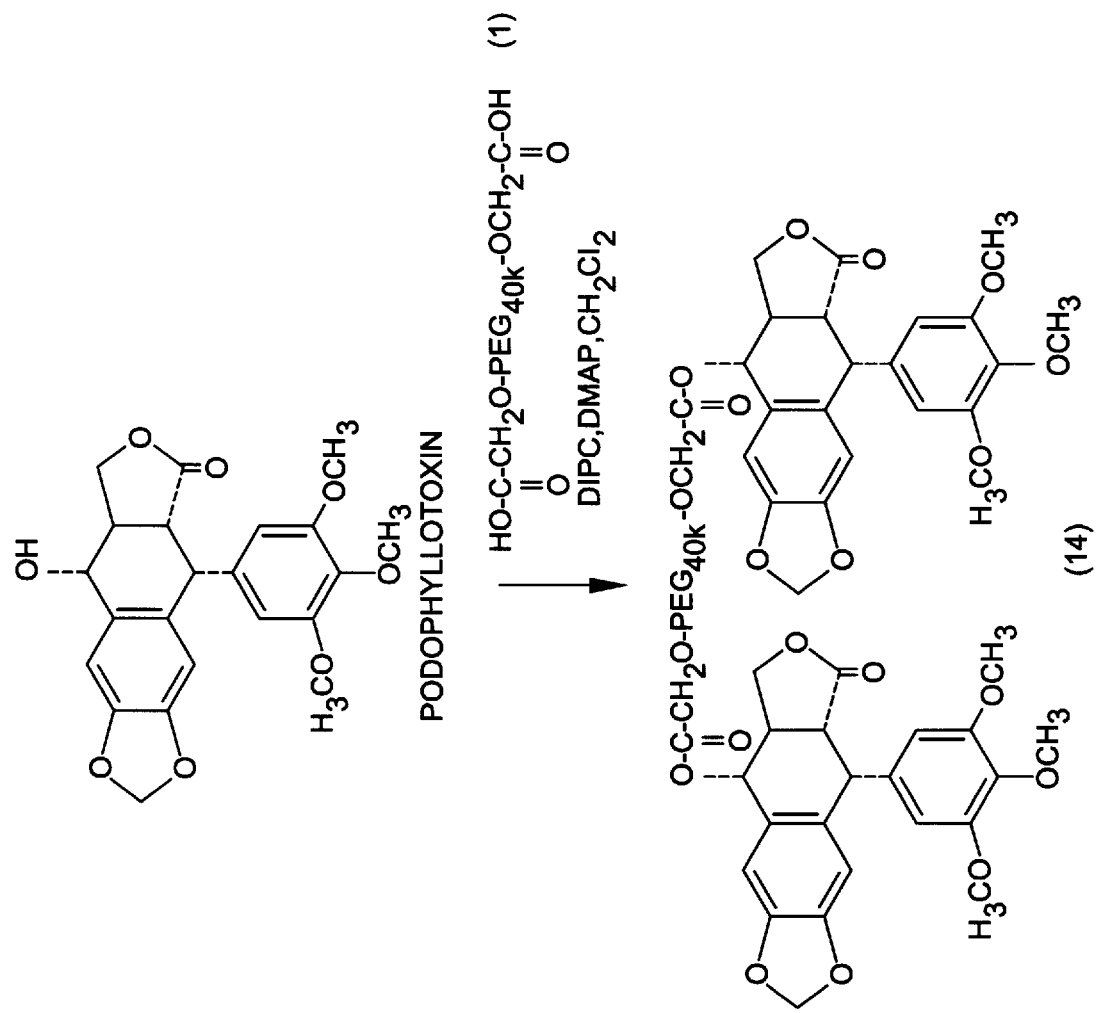
FIG. 7 is a schematic representation of the reactions carried out in accordance with Example 17.

Still further examples of ester-linked polymeric camptothecin prodrugs are the acyl ester derivatives such as those shown in FIG. 5. Details concerning the reaction schemes and conditions are provided in Section D, below, the attached figures, and in the Examples.

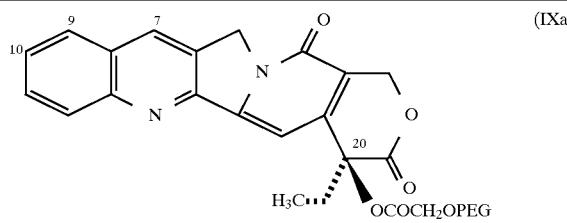

Pro-20(S)-Camptothecin

| Pro-Camptothecin analogues | Position | | |
|---|---|---|---|
| | 7 | 9 | 10 |
| Pro-Topotecan | H | $CH_2N(CH_3)_2$ | OH |
| Pro-CPT-11 | $-CH_2-CH_3$ | H | 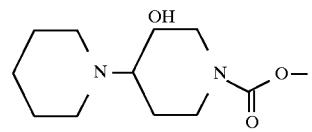 |

In addition to the foregoing camptothecin analogs, it has been surprisingly found that new 20(S)camptothecin-mono-PEG ester compounds are formed when a diacid PEG is used. Contrary to what was expected, the polymer diacid forms the monoester with the camptothecin to a greater extent (>90% than would be predicted) under conditions which would seemingly provide predominately bis-analogs. The alpha terminus of the polymer has been converted to camptothecin-PEG ester and the omega terminus was found to be substantially converted from the acid to an acyl dialkyl urea, depending on the dialkyl carbodiimide employed to effect conjugation. As shown in Example 15, this derivative was also shown to have antitumor activity in vivo. Furthermore, upon NMR inspection, it was determined that cross-linking was negligible.

Thus, in this aspect of the invention, the camptothecin analogs have the formula:

$$D-Y'-\overset{\overset{Y}{\|}}{C}-CH_2-M-R-Z^3 \quad \text{(IXb)}$$

wherein:

D, Y, Y', M and R are the same as that set forth above; and $$Z^3 \text{ is } D''-\overset{\overset{Y}{\|}}{C}-CH_2-M-$$

where D" is preferably selected from the group consisting of dialkyl ureas, $C_{1-4}$ alkoxy or carboxylic acids.

3. Additional Biologically-Active. Moieties

In addition to the foregoing molecules, the prodrug formulations of the present invention can be prepared using many other compounds. For example, biologically-active compounds such as etoposide (VePesid™, Bristol Myers, New York, N.Y.), podophyllotoxin and related compounds can be included. The prodrug ester is formed at the C-4' hydroxy for etoposide and at the C-4 hydroxy for podophyllotoxin. The parent compounds selected for prodrug forms need not be substantially water-insoluble, although the polymer-based prodrugs of the present invention are especially well suited for delivering such water-insoluble compounds. Other useful parent compounds include certain low molecular weight biologically active proteins, enzymes and peptides, including peptido glycans, as well as other anti-tumor agents, cardiovascular agents, anti-neoplastics, anti-infectives, anti-fungals, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like are also contemplated.

The foregoing is illustrative of the biologically active moieties which are suitable for the prodrugs of the present invention. It is to be understood that those biologically active materials not specifically mentioned but having suitable ester-forming groups are also intended and are within the scope of the present invention. It is also to be understood that the prodrug conjugates of the present invention may also include compounds containing not only one equivalent of drug and polymer but also a moiety which does not effect bioactivity in vivo. For example, it has been found that in some instances, in spite of reacting diacids with drug molecules having a single linkage point, the reaction conditions do not provide prodrugs with two equivalents of drug per polymer. On the contrary, the prodrugs contain only one equivalent of drug per polymer. By-products of the reactants such as acyl ureas can be formed. Furthermore, it has also been found that in spite of the reaction with a bis-activated polymer, the prodrugs are remarkably free of crosslinked species.

The only limitation on the types of molecules suitable for inclusion herein is that there is at least one position on which the hydrolyzable linkage can be attached, so that after prodrug administration, the prodrug can regenerate sufficient quantities of the parent compound in vivo.

D. SYNTHESIS OF PRODRUGS

Synthesis of specific prodrugs is set forth in the Examples. Generally, however, the prodrugs are prepared by 1) providing an activated polymer, such as a PEG-acid or PEG-diacid and a parent compound having a position thereon which will allow a hydrolyzable linkage to form, 2) reacting the two substituents in an inert solvent such as methylene chloride, chloroform or DMF in the presence of a coupling reagent such as 1,3-diisopropylcarbodiimide or any suitable dialkyl carbodiimide available from Sigma Chemical or synthesized using known techniques and a base such as dimethylaminopyridine, diisopropyl ethylamine, pyridine, triethylamine, etc. at a temperature from 0° C. up to 22° C. (room temperature). Alternative Specific syntheses are provided in the examples.

E. METHODS OF TREATMENT

Another aspect of the present invention provides methods of treatment for various medical conditions in mammals. The methods include administering to the mammal in need of such treatment, an effective amount of a prodrug, such as a taxol 2'-PEG ester, which has been prepared as described herein. The compositions are useful for, among other things, treating neoplastic disease, reducing tumor burden, preventing metastasis of neoplasms and preventing recurrences of tumor/neoplastic growths in mammals.

The amount of the prodrug administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug taxanes are administered in amounts ranging from about 5 to about 500 mg/m$^2$ per day, based on the amount of the taxane moiety. Camptothecin, etoposide and podophyllotoxin prodrugs are also administered in amounts ranging from about 5 to about 500 mg/$^2$ per day. The range set forth above is illustrative and those skilled in the art will determine the optimal dosing of the prodrug selected based on clinical experience and the treatment indication.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. In preferred aspects of the invention, however, the prodrugs are parenterally administered to mammals in need thereof

F. EXAMPLES

The following examples serve to provide further appreciation of the invention but are not meant in any way to restrict the effective scope of the invention. The numbers shown in bold in parentheses in Examples 1–17 correspond to the compounds shown in the schematic diagrams set forth in FIGS. 1–7.

Example 1

PEG (40 kDa) dicarboxylic acid (1):

A solution of PEG diol (50 g, 1.3 mmol) in toluene (750 mL) was azeotroped with the removal of 150 mL of distillate. The reaction mixture was cooled to 30° C., followed by the addition of 1M potassium t-butoxide in t-butanol (4 mL, 4.0 mmol). The resulting mixture was stirred for 1 h at room temperature followed by the addition of ethyl bromo acetate (1.6 mL, 14 mmol). The solution was heated to reflux, and then stirred at room temperature for 18 h. The reaction mixture was filtered through celite and the solvent was removed in vacuo. The residue was recrystallized from methylene chlorideether to give the PEG (40 kDa) diethyl ester (45.2 g, 86%). $^{13}$C NMR: C=O, 170.9 ppm.

A solution of diester (20 g, 0.5 mmol), in 1N sodium hydroxide (100 mL) was stirred at room temperature for 4 h. The basic solution was cooled in an ice bath, adjusted to pH 3.0 with 2N HCl, and extracted three times with methylene chloride. The pooled extracts were washed with water, concentrated to 15 mL, and the solution was added to ethyl ether (200 mL) with stirring. The precipitate was filtered, washed with ether, dried and crystallized from 2-propanol to yield (16.9 g, 84%) of diacid (1).

$^{13}$C NMR: 68.05,68.1–71(PEG)170.93.

Example 2

Taxol-2'-PEG$_{40kDa}$ Ester(2+3):

PEG$_{40kDa}$ diacid (1,5 g, 0.125 mmol) was dissolved in 20 mL of anhydrous methylene chloride at room temperature and to this solution at 0° C. were added DIPC (52.2 μL, 0.34 mmol), DMAP (64 mg, 0.523 mmol) and taxol (292 mg, 0.34 mmol) at 0° C. The reaction mixture was allowed to warm to room temperature and left for 16 hrs. The solution was washed with 0.1N HCl, dried and evaporated under reduced pressure to yield a white solid which was recrystallized from 2-propanol. The product (80–90% yield) was found to be a mixture of di (2) and monoester (3). Structures of these compounds were confirmed by $^{13}$C and $^1$H NMR analysis. The ratio of mono to diester was found to be 1:2 as determined by the UV assay as described below. Separation of the ester mixture was not attempted, as it is difficult to differentiate between PEG derived compounds of similar molecular weights using standard chromatographic and crystallization techniques. For the purposes of in vitro and in vivo testing the mixture was used as such.

$^1$HNMR(270 MHz,CDCl$_3$) δ 1.1(s), 1.19(s), 1.21(s), 1.26 (s), 1.39(s), 1.42(s), 1.75(s), 1.8(s), 1.9(s), 2.2(s), 2.24(s), 2.51(s), 2.54(s), 3.39(m), 3.59–3.71(br s,PEG), 3.91(s), 4.2–4.4(m), 4.5–4.6(m), 5.0(d,J=8 MHz)), 5.6(m), 5.8(d,J= 5.4 MMz),6(m), 6.2–6.4(m), 7.3(s), 7.4–7.7(m), 7.8(d,J=8.1 MHz), 8.2(d,J=8.1 MHZ). $^{13}$C NMR (270 MHz,CDCl$_3$) δ9.40, 14.61, 20.0, 20.64, 21.92, 22.0, 22.54, 26.63, 35.37, 42.0, 42.99, 45.39, 47.0, 52.71, 58.30, 68.0, 70.38, 71.91, 74.19, 74.91, 75.39, 78.91, 80.86, 84.23, 126.72, 127.10, 128.38, 128.56, 128.88, 129.04, 130.05, 131.67, 132.61, 133.58, 136.73, 142.54, 152.7, 166.80, 167.17, 167.66, 169.65, 169.82, 170.98, 203.61.

Example 3

Analysis of taxol-PEG$_{40kDa}$ Ester(2+3):

The UV absorbance of native taxol in methylene chloride was determined at 227 nm for five different concentrations ranging from 4 to 21 μM. From the standard plot of absorbance vs. concentration, the absorption coefficient for taxol (2+3) was calculated to be 2.96×10$^4$ Mol$^{-1}$Cm$^{-1}$. Taxol-PEG$_{40kDa}$ ester was dissolved in methylene chloride at an approximate concentration of 4 μM, and the UV absorbance of these compounds at 227 nm was determined. Using this value, and employing the absorption coefficient obtained from above, the concentration of taxol in the sample was determined. Thus, dividing this value by the taxol-PEG ester concentration provided the percentage of taxol in the esters.

Example 4

Camptothecin-20-PEG$_{40kDa}$ Ester(4a+4b):

PEG$_{40kDa}$ diacid (1), 11.5 g, 0.287 mmol,) was dissolved in 200 mL of anhydrous methylene chloride at room temperature and to this solution at 0° C. were added DIPC (0.175 mL, 1.15 mmol), DMAP (140 mg, 1.15 mmol) and camptothecin (399 mg, 1.15 mmol) at 0° C. The reaction mixture was allowed to warm to room temperature after 2 hours and left for 16 hrs. The solution was concentrated to about 100 mL and filtered through celite and the filtrate was washed with 0.1N HCl, dried(anhyd.MgSO$_4$)and evaporated under reduced pressure to yield a white solid which was recrystallized from DMN/ether, followed by washing with 2-propanol. The product (9.52 g, 82% yield) was found to be a mixture of mono and diester (4a and 4b) with the opposite end of the monoester (4a) having an N-acyl disopropylureido group. The structure of this compound was confirmed by $^{13}$C NMR analysis. Determination of % camptothecin in the product using the UV method of the previous example indicated 1.35 eq. of camptothecin per PEG molecule. This indicates the ratio of mono to diester to be 1.8:1.

$^{13}$C NMR (270 MHz,CDCl$_3$) δ 7.25, 19.6, 22.3, 31.4, 42.5, 46.38, 48.68, 53.48, 62.8, 66, 67–71(PEG), 75, 94.21, 118.8, 127.2, 127.4, 127.5., 127.65, 128.5, 129.5, 130.5, 144.48, 145.67, 151.5, 152.7, 156.53, 166.2, 168.78.

Example 5

PEG$_{40kDa}$Glycine(5):

PEG$_{40kDa}$ diacid (1, 9.5 g, 0.23 mmol) was dissolved in 20 mL of anhyd. methylene chloride at room temperature and to this solution at 0° C. were added DIPC (141 μL, 0.92 mmol), DMAP (197 mg, 1.6 mmol) and glycine t-butyl ester (176.4 mg, 0.92 mmol) at 0° C. The reaction mixture was allowed to warm to room temperature after 3 hours and left for 16 hours. The solution was washed with 0.1N HCl, dried and evaporated under reduced pressure to yield PEG$_{40kDa}$glycine t-butyl ester as a white solid which was dissolved in a mixture of methylene chloride(50 ml)and trifluoroacetic acid (25 ml ) at 0° C. for overnight. Solvent was removed and the solid was recrystallized from methylene chloride/ether to give (5) (7.1 g, 75%).

$^{13}$C NMR (270 MHz,CDCl$_3$) δ 39.42,69.59,70.19,169.39, 169.46.

Example 6

20-PEG$_{40kDa}$glycinylCamptothecin(6):

PEG$_{40kDa}$glycine (5, 2 g, 0.05 mmol) was dissolved in 20 mL of anhydrous methylene chloride at room temperature and to this solution at 0° C. were added DIPC (38.1 μL, 0.26 mmol), DMAP (92 mg, 0.75 mmol) and 20-(S)-campthotecin (85 mg, 0.25 mmol). The reaction mixture was allowed to warm to room temperature and left for 16 hours. The solution was washed with 0.1N HCl, dried and evaporated under reduced pressure to yield 6 as a white solid which was recrystallized from 2-propanol (1.4 g, 69%).

Example 7

2'PEG$_{40kDa}$glycinyl-taxol(7):

PEG$_{40kDa}$ glycine (5, 2 g, 0.05 mmol) was dissolved in 20 mL of anhydrous methylene chloride at room temperature and to this solution at 0° C. were added DIPC (6.5 μL, 0.1 mmol), DMAP (8.1 mg, 0.1 mmol) and taxol (86 mg, 0.1 mmol) at 0° C. The reaction mixture was allowed to warm to room temperature and left for 16 hrs. The solution was washed with 0.1N HCl, dried and evaporated under reduced pressure to yield 7 as a white solid which was recrystallized from 2-propanol.

Example 8

20-bromoacetyl-camptothecin(8):

To a suspension of camptothecin,(1 g, 2.87 mmol) in CH$_2$Cl$_2$ (700 ml) was added bromoacetic acid(1.2 g, 8.61 mmol), diisopropylcarbodiimide (DIPC, 1.3 ml, 8.61 mmol) and dimethylaminopyridine (DMAP, 0.7 g, 5.74 mmol) at 0° C. and stirring was continued for 4 hours. The resulting yellow solution was concentrated to about 100 ml and washed with 1N hydrochloric acid (10 ml×2), followed by 1% aq. sodium bicarbonate solution (10 ml×2). Organic layer was dried (anhyd.MgSO$_4$)and evaporated in vacuo to give a yellow solid. Methanol (10 ml) was added, and the slurry filtered to yield 8 (0.9 g, 67%) as a yellow solid.

$^1$H NMR(270 MHz,CDCl$_3$) δ 1.0(t), 1.7(s), 2.1–2.5(m), 4.0(q), 5.3(s), 5.4–5.8(dd), 7.25(s), 7.3(s), 7.6–8.5(m). $^{13}$C NMR (270 MHz,CDCl$_3$) δ 7.51, 24.97, 31.77, 49.97, 67.16, 76.53, 95.73, 120.29, 128.05, 128.39, 129.64, 130.65, 131.17, 144.94, 146.48, 148.84, 152.18, 157.24, 165.97, 166.8.

Example 9

20-Iodoacetyl-camptothecin(9):

To a suspension of camptothecin, (1.06 g, 3.04 mmol) in CH$_2$Cl$_2$ (700 ml) was added iodoacetic acid (1.2 g, 8.61 mmol), diisopropylcarbodiimide (DIPC, 1.4 ml, 9.13 mmol) and dimethylaminopyridine (DMAP, 0.74 g, 6.08 mmol) at 0° C. and stirring was continued for 4 hours. The resulting yellow solution was concentrated to about 100 ml and washed with 1N hydrochloric acid (10 ml×2), followed by 1% aq. sodium bicarbonate solution (10 ml×2). Organic layer was dried (anhyd.MgSO$_4$) and evaporated in vacuo to give a yellow solid to which methanol (10 ml) was added and the slurry was stirred and filtered to yield 9 as yellow solid (1.25 g, 80%).

$^1$H NMR(270 MHz,CDCl$_3$) δ 1.0(t), 2.1–2.6(m), 3.7–4.0 (dd), 5.2(s), 5.4–5.8(dd), 7.2–8.5(m). $^{13}$C NMR (270 MHz, CDCl$_3$) δ 7.54, 31.77, 49.98, 67.17, 95.88, 120.32, 128.02, 128.17, 128.41, 129.76, 130.60, 131.12, 145.03, 146.40, 148.91, 152.28, 157.28, 166.98, 167.35.

Example 10

Reaction of 20-bromoacetyl-camptothecin with PEG$_{40kDa}$ dicarboxylic- acid: (10):

PEG$_{40kDa}$dicarboxylic-acid (1, 5 g, 0.125 mmol) was azeotroped in 100 ml of toluene for 1.5 hr with the removal of 50 ml distillate. To the above solution, was added 1.0M potassium tert-butoxide (0.274 ml, 0.28 mmol) in t-butanol. The reaction solution was refluxed for 1.5 hours followed by removal of the solvent in vacuo to give the dipotassium salt of PEG$_{40kDa}$ dicarboxylicacid. To a solution of the dipotassium salt (1.17 g, 0.007 mmol) in DMSO (10 ml) was added camptothecin-20-bromoacetate (41 mg, 0.0873 mml) and the resulting mixture was warmed to 40° C. to obtain a clear solution. Stirring was continued overnight at room temperature and ether (10 ml) was added. The solid precipitated was filtered and redissolved in methylene chloride. Organic layer was washed with water (5 ml), dried (anhyd.MgSO$_4$) and the solvent was evaporated in vacuo to give a solid which was recrystallized from 2-propanol to give 10 (0.9 g, 76.3%). 1.6eq. of camptothecin per PEG molecule was obtained by the UV method indicating that probably some mono ester was present in the diester product.

$^{13}$C NMR (270 MHz,CDCl$_3$)δ: 7.02, 31.17, 49.58, 53.35, 59.77, 66–73 (PEG), 94.68, 119.41, 127.16, 127.44, 127.53, 127.96, 128.77, 129.77, 130.29, 144.06, 145.84, 148.05, 151.20, 156.14, 166.36, 169.08.

Example 11

Podophyllotoxin-4-glycinylPEG$_{40kDa}$ (11):

PEG$_{40kDa}$ glycine (5, 2 g, 0.05 mmol) was dissolved in 20 mL of anhydrous methylene chloride at room temperature and to this solution at 0° C. were added DIPC (27.3 μL, 0.18 mmol), DMAP (21.9 mg, 0.18 mmol) and podophyllotoxin (110 mg, 0.25 mmol) at 0° C. The reaction mixture was allowed to warm to room temperature and left for 16 hours. The solution was washed with 0.1N HCl, dried and evaporated under reduced pressure to yield 11 as a white solid which was recrystallized from 2-propanol.

Example 12

TAXOL 2'-PEG 5,000 MONOESTER

A. m-PEG 5,000 CARBOXYLIC ACID PREPARATION

The procedure of Example 1 was repeated except that m-PEG-OH 5,000 was used instead of the PEG diol.

B. TAXOL-2' m-PEG 5,000 MONOESTER PREPARATION

PEG 5,000 acid was azeotroped before use. The PEG 5,000 acid (625 mg, 0.125 mmol) was dissolved in 20 ml of anhydrous methylene chloride at room temperature. The above solution was treated with 1,3-dilsopropylcarbodiimide (26 μl, 0.17 mmol), 4-dimethylaminopyridine (32 mg, 0.26 mmol) and taxol (146 mg, 0.17 mmol) at 0° C. The reaction solution was warmed to room temperature after 30 minutes and kept at that temperature for 16 hours. The reaction mixture was then washed with 0.1N HCl, dried and evaporated to yield a white solid which was crystallized from 2-propanol to yield 585 mg (80% yield) of pure product.

Example 13

PREPARATION OF 20-CAMPTOTHECIN m-PEG 5,000 ESTER

A. PEG 5,000 CARBOXYLIC ACID PREPARATION

The procedure of Example 1 was repeated except that m-PEG-OH 5,000 was used instead of the PEG diol.

B. 20-CAMPTOTHECIN m-PEG 5,000 ESTER PREPARATION

The PEG 5,000 acid was azeotroped in toluene prior to use. The PEG 5,000 acid (400 mg, 0.079 mmol) was dissolved in 10 ml of anhydrous methylene chloride at room temperature before being treated with 1,3-diisopropyl carbodiimide (18.1 μl, 0.119 mmol), 4-dimethylamino pyridine (14.5 mg, 0.119 mmol) and (S)-(+)-camptothecin (41.32 mg, 0.119 mmol) at 0° C. The action solution was warmed to room temperature over 30 minutes and kept at that temperature for 16 hours. The reaction solution was then washed with 0.1N HCl, dried and evaporated to yield an off-white solid which was purified by chromatography (silica gel, MeOH/CH$_2$C$_2$). The purified material was crystallized from CH$_2$Cl$_2$/ether.

Example 14

IN VITRO BIOASSAY

In this example, a series of in vitro assays were conducted to determine the IC$_{50}$ for unmodified taxol, 2'-PEG 5,000-taxol (Example 12), unmodified camptothecin, 20-camptothecin PEG 5,000 ester (Example 13) and several of the high molecular weight prodrugs prepared as set forth above. The unmodified taxol was obtained from PHYTOPharmaceuticals, Inc. and the unmodified camptothecin was obtained from Sigma Chemical Co.

All compounds were independently tested against the P388/0 (murine lymphoid neoplasm, Southern Research Institute), HT-29 (human colon carcinoma), T-47D (human breast adeno carcinoma), SW-48 (human colon adeno carcinoma), A549 (human lung adeno carcinoma) cell lines.

The P388/0 cells were grown in RPMI 1640 medium (Whittaker Bioproducts, Walkersville, Md.)+10% FBS (Hyclone Inc., Logan, Utah). The HT-29 cells were grown in DMEM (GIBCOBRL)+10% FBS (Hyclone, Inc.). The SW48 cells were grown in Leibowitz's L-15 medium (GIBCOBRL)+10% FBS. The A549 cells were grown in DMEM/F-12 (Biowhitaker)+10% FBS (Heat inactivated). The T47-D cells were grown in RPMI1640+10% FBS+ Insulin (10 mglml). Bioassays were performed in their respective media containing antibiotics and fungizone.

Camptothecin, taxol and Podophyllotoxin were dissolved in DMSO and diluted to the appropriate concentration in culture media. PEG-Camptothecin, PEG-taxol and PEGPpodophyllotoxin prodrugs were dissolved in water and diluted to the appropriate concentrations in culture media.

The assays were performed in duplicate in 96-well microtiter cell culture plates. Two fold serial dilution of the compounds were done in the microtiter plates. Cells were detached by incubating with 0.1% Trypsin/Versene at 37°. Trypsin was inactivated by adding the appropriate media for each cell line containing 10% FBS. To each well of the microtiter plates, 10,00 cells were added. After three days, cell growth was measured by addition of a metabolic indicator dye, Alamar Blue, according to the manufacturer's protocol. The $IC_{50}$ value for each test compound was determined and compared to the $IC_{50}$ for the appropriate reference compound.

| Compound | $IC_{50}(nM)$ | | | | |
|---|---|---|---|---|---|
| | P388 | HT-29 | T-47D | SW-48 | A549 |
| taxol | 6–12 | | | | |
| taxol-2-PEG5kDa ester (12) | 15 | | | | |
| taxol-2-glycinyl PEG40kDa ester (7) | 14 | | | | |
| taxol-2-PEG40kDa ester (2 + 3) | 10 | | | | |
| Camptothecin | 7–16 | 40–80 | 14–19 | 35–88 | 300 |
| Camptothecin-20-PEG5kDa ester (13) | 33–48 | 100–362 | | | |
| Camptothecin-20-PEG40kDa ester (4a + 4b) | 17–27 | 67 | 34 | 194 | 823 |
| Camptothecin-20-acyloxy PEG40kDa ester (10) | 15 | | | | |
| Camptothecin-20-glycinyl PEG40kDa ester (6) | 34 | | | | |
| Podophyllotoxin | 7 | 21 | 24 | 15 | 24 |
| Podophyllotoxin-4-glycinyl PEG40kDa ester (11) | 11 | | | | |
| Podophyllotoxin-4-PEG40kDA ester (14) | 24 | 55 | 39–60 | 116–142 | 97–127 |

P-388 - Murine leukemia cell line
HT-29 - Human colon carcinoma cell line
T-47D - Human breast adeno carcinoma cell line
SW-48 - Human colon adeno carcinoma cell line
A549 - Human lung adeno carcinoma cell line Referring now to the table, it can be seen that both the low and the relatively high molecular weight polymer prodrugs compare favorably to unmodified forms of the drug. Applicants, however, have surprisingly found that in vitro results with the low molecular weight polymer prodrugs were not consistent with the results obtained when in vivo tests were undertaken. See Example 15 below.

Example 15

IN VIVO STUDY

In this Example, 40 female mice, approximately 8–10 weeks old at the beginning of the experiment, and obtained from Charles River Laboratories, Wilmington, Mass. were broken up into 4 groups of 10. The mice were infected with the P388/0 murine lymphoid neoplasm to determine the in vivo effects of prodrugs prepared in accordance with the present invention. This experiment followed the procedure of Ward, et al. set forth in Cancer Chemother. Pharmacol., 31:255–257 (1992), the contents of which are incorporated by reference herein. The purpose of the study was to determine the ability of the prodrug to increase the life span of the mice.

Each mouse was implanted with $5 \times 10^5$ P388/0 cells on day zero and treated with the respective drug for five consecutive days. Ten mice were injected with vehicle (50/50 Cremophor EL/ethanol) alone and ten mice were untreated (controls). The final endpoint for the example is survival. The resulting data are presented below:

| DRUG | DOSE/DAY $\mu M$ | TOTAL DOSE $\mu M$ | TIME TO 50% SURVIVAL DAYS | MEAN TIME TO DEATH DAYS |
|---|---|---|---|---|
| CONTROL-UNTREATED | 0 | 0 | 12.5 | 12.6 ± 1.2 |

-continued

| DRUG | DOSE/DAY $\mu M$ | TOTAL DOSE $\mu M$ | TIME TO 50% SURVIVAL DAYS | MEAN TIME TO DEATH DAYS |
|---|---|---|---|---|
| CONTROL-VEHICLE | 0 | 0 | 12.5 | 12.7 ± 1.3 |
| Taxol | 0.35 | 1.75 | 18 | 18.7 ± 1.3 |
| 2'-PEG 5,000 Taxol (Ex 12) (cmpd 12) | 0.35 | 1.75 | 12.9 | 14.1 ± 2.3 |
| 2'-PEG 40,000 Taxol (Ex 2) (cmpd 2 + 3) | 0.35 | 1.75 | 19.0 | 20.3 ± 1.1 |
| Taxol | 1.05 | 5.25 | 7.25 | 7.8 ± 1.40 |
| 2'-PEG 5,000 taxol (Ex 12) (cmpd 12) | 1.05 | 5.25 | 15.0 | 15.7 ± 2.1 |
| 2'-PEG 40,000 Taxol (Ex 12) (cmpd 2 + 3) | 1.05 | 5.25 | 5.75 | 6.3 ± 0.5 |
| 20 Campto.-PEG 40,000 (Ex 4) (cmpd 4a + 4b) | 0.35 | 1.75 | 24.0 | 24.9 |
| 20 Campto.-PEG 40,000 (Ex 4) (cmpd 4a + 4b) | 0.70 | 3.50 | 10.0 | 29.0 |

The data can be summarized as follows: all compounds increased the life span of the mice versus the controls at doses of 1.75 $\mu$zmoles/mouse. It was surprisingly found that the 2'-PEG 5,000 was significantly less effective than taxol (p<0.001) at this dosage. Even at triple the dose, the PEG 5,000 prodrug (5.25 $\mu$zmoles/mouse) was still significantly less effective than the parent compound (taxol at 1.75 $\mu$moles/mouse). On the other hand, the prodrug prepared with PEG 40,000 diacid is approximately equivalent to the parent compound at doses of 1.75 $\mu$moles/mouse, (extended survival due to anti-tumor activity) and doses of 5.25 $\mu$moles/mouse (shortened survival due to toxicity). While Applicants are not bound by theory, it is believed that the unique combination of higher molecular weight polymer and the rapid rate of hydrolysis of the particular ester linkage allow therapeutic amounts of the parent compound to be generated before the prodrug is cleared from the body.

Separately, it was observed that the 20-camptothecin-PEG 40,000 substantially increased survival time when compared to the controls.

Example 16

$T_{1/2}$ HYDROLYSIS TIME

In this example, the $t_{1/2}$ for hydrolysis of an ester-based prodrug linkage prepared in accordance with the present invention was compared to the ester linkage disclosed in PCT WO93/24476. In particular, the 2'-PEG ester of Example 2 was compared to the prodrug designated as compound (7) in the PCT publication except that mPEG 5,000 was used to prepare the PEG acid.

The prodrug compositions of Example 2 and the comparative compound described above were thus prepared to have the following substituents in the 2' position:

| | Taxol 2'-substitution |
|---|---|
| Example 2: | O—C(O)—CH$_2$—O—(CH$_2$—CH$_2$O)$_m$—CH$_2$—C(O)-0 |
| Comparative: | O—C(O)—CH$_2$CH$_2$—C(O)O—(CH$_2$—CH$_2$O)$_n$—CH$_3$ | m = 909, such that PEG has a MW of 40,000
n = 114, such that PEG has a MW of 5,000.

The comparative ester-based prodrug was prepared in the following manner:

a. Comparative 2' mPEG-taxol ester synthesis

MPEG MW 5,000 succinic acid (SS acid) prepared as reported in the literature (Abuchowski, A, et al., *Cancer Bichem. Biophys.* 7,175–186 (1984), (300 mg, 0.0588 mmol) and taxol (75.3 mg, 0.0882 mmol) were azeotroped with toluene (40 ml) for 2 hours. 20 ml of toluene was removed and the mixture was cooled to room temperature and the solvent was removed under reduced pressure using a rotary evaporator. The residue was dissolved in anhydrous methylene chloride (10 ml) followed by the addition of diisopropylcarbodiimide (11.1 mg, 0.0882 mmol) and dimethyl aminopyridine (10.8 mg, 0.002 mmol). The reaction mixture was stirred at room temperature overnight. The mixture was then washed with 0.1N HCl and the solvent was dried (anhydrous sodium sulfate) and removed by rotary evaporator. The resulting residue was crystallized from 2-propanol to give 252 mg of solid material which was shown to be a mixture of two compounds, the required product and a free PEG component. This mixture was purified by Prep HPLC using a 47 mm×300 mm C8 cartridge column (Waters PrepPack) under a radial pressure of 600 psi, using methanol water gradient system as the mobile phase. The pure product ( 40 mg) was characterized by proton NMR and HPLC.

The rate of hydrolysis for each compound was determined by the following tests:

b. Hydrolysis of bis taxol 2' ester of PEG 40,000 diacid in phosphate buffer pH 7.3

The ester of Example 2 was dissolved in pH 7.3 phosphate buffer at a concentration of 20.3 mg/ml (equivalent to 0.5 mg/ml of taxol based on UV assay) and kept at 37° C. Thereafter, 100 μl samples were withdrawn from the solution at one hour intervals and injected directly into HPLC. The area under the taxol peak was compared with a standard curve generated for taxol (amount vs peak area). Accordingly, the amount of taxol formed by hydrolysis was calculated. In this case, the half life of the prodrug, i.e., the time taken for 50% of prodrug to hydrolyze was found to be 5–6 hours.

c. Hydrolysis of bis taxol 2' ester of PEG 40,000 diacid in rat plasma

The ester of Example 2 was dissolved in rat plasma, physiological pH: approximately 7.3 (with unspecified esterase activity) at a concentration of 6 mg/ml (equivalent to 0.15 mg/ml of taxol based on UV assay) and kept at 37° C. Thereafter, 100 μl portions were withdrawn at regular intervals and extracted with 3×500 μl of ethyl acetate. The organic layers were combined and evaporated to dryness. The residue was dissolved in 50 μl of methanol and injected into a HPLC. The area under the taxol peak was compared to the standard curve generated for taxol and the amount of taxol formed by hydrolysis was calculated. In this case, the half life was determined to be 1.6 hours, indicating that substantial esterase activity was present.

d. Hydrolysis of bis taxol 2' ester of PEG 40,000 diacid in distilled water

The procedure of Example 16c. was repeated except that distilled water was used in place of rat plasma. The half life for the product of Example 2 was determined to be greater than 96 hours.

e. Hydrolysis of comparative 2' mPEG taxol esters

The procedures of steps b, c and d were repeated using the comparative taxol prodrug produced in step a. The results are set forth below:

| | $T_{1/2}$ HYDROLYSIS (HRS) | | |
|---|---|---|---|
| PRODRUG | PBS BUFFER (pH 7.3) | RAT PLASMA (pH 7.3) | DISTILLED WATER (pH 6.8) |
| EXAMPLE 2 | 5.0 | 1.6 | >96 |
| COMPARATIVE | >96 | >7 | >96 |

As can be seen from the table, the prodrug formulations of the present invention have substantially quicker rates of hydrolysis than that shown in the prior art. In distilled water, pH 6.8, it can be seen that both compounds are essentially stable. The rate enhancement is evident and useful for in vivo environments where esterases are present (rat plasma) or not (PBS buffer pH 7.3). This regeneration of the parent compound affords benefits which are apparent only after conducting in vivo analyses of PAO prodrug compounds.

As was demonstrated in Example 14, the results of the in vitro tests suggest that hydrolysis of the polymer linkage was sufficient to effect cytotoxicity. The in vivo tests of Example 15, however, clearly show that regeneration of sufficient amounts of the parent compound during the time the prodrug remains in circulation is a key to providing an effective prodrug composition.

Thus, ester linkages with relatively long $t_{1/2}$ hydrolysis fail to provide useful PAO-based prodrugs because most of the parent compound is excreted before being released in vivo. This effect is especially apparent when relatively low molecular weight polymers are used.

Example 17

Podophyllotoxin-4- PEG$_{40kDa}$ ester (14):

The procedure of Example 2 was repeated but wit podophyllotoxin instead of taxol. The product was shown in FIG. 7 (Compound 14).

We claim:

1. A composition comprising the formula:

$$D-Y'-\overset{\overset{Y}{\|}}{C}-CH_2-M-R \quad (I)$$

wherein:
D is a residue of a biologically active moiety having undergone an esterification reaction;
M is X or Q;
X is an electron withdrawing group;
Q is a moiety containing a free electron pair positioned five or six atoms from Y';
Y and Y' are independently O or S;
R is a substantially non-antigenic polymer.

2. The composition of claim 1, wherein R further comprises a capping group Z.

3. The composition of claim 2, wherein Z is one of OH, a $C_{1-4}$ alkyl moiety or $$D'-Y'-\overset{\overset{Y}{\|}}{C}-CH_2-M-;$$

wherein D' is the same as D or a different biologically active moiety.

4. The composition of claim 1, wherein X is selected from the group consisting of O, OC(O)CH$_2$, N(L)C(O), C(O)N(L), C(O), N(L), S, SO and S0$_2$;
wherein L is selected from the group consisting of H, $C_{1-8}$ alkyls, cycloalkyls, aryls, and aralkyls.

5. The composition of claim 1, wherein Y and Y' are O.

6. The composition of claim 1, wherein X is O.

7. The composition of claim 1, wherein X is —NHC(O).

8. The composition of claim 1, wherein Q is selected from the group consisting of $C_{2-4}$ alkyls, cycloalkyls; aryl, aralkyl groups substituted with a member of the group consisting of NH(L), OH and SH,
where L is selected from the group consisting of H, $C_{1-8}$ alkyls, aryls and aralkyls.

9. The composition of claim 8, wherein Q is selected from the group consisting of —CH$_2$—C(O)—N(H)—, and ortho-substituted phenyls.

10. The composition of claim 1, wherein said substantially non-antigenic polymer comprises polyethylene glycol.

11. The composition of claim 2, wherein Z is CH$_3$.

12. The composition of claim 2, wherein Z is $$D-Y'-\overset{\overset{Y}{\|}}{C}-CH_2-X-.$$

13. The composition of claim 2, wherein Z is $$D-Y'-\overset{\overset{Y}{\|}}{C}-CH_2-Q-.$$

14. The composition of claim 1, wherein said substantially non-antigenic polymer has a molecular weight of from about 20,000 to about 80,000.

15. The composition of claim 14, wherein said substantially non-antigenic polymer has a molecular weight of from about 25,000 to about 45,000.

16. The composition of claim 15, wherein said substantially non-antigenic polymer has a molecular weight of from about 30,000 to about 42,000.

17. The composition of claim 1, wherein D is selected from the group consisting of taxol, taxane and taxotere, and Y' is attached to the 2' position of said D.

18. The composition of claim 1, wherein D is selected from the group consisting of camptothecin, etoposide and podophyllotoxin.

19. The composition of claim 1, wherein D is selected from the group consisting of biologically active proteins, enzymes, peptides, anti-tumor agents, cardiovascular agents, anti-neoplastics, anti-infectives, anti-fungals, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, and vasoconstricting agents.

20. A method of preparing a composition of the formula:

$$D-Y'-\overset{\overset{Y}{\|}}{C}-CH_2-M-R \quad (I)$$

wherein:
D is a biologically active moiety;
M is X or Q;
X is an electron withdrawing group;
Q is a moiety containing a free electron pair positioned five or six atoms from Y';
Y and Y' are independently O or S; and
R is a polyalkylene oxide;
comprising reacting a biologically active moiety, D, with a polymer of the formula:

$$Z'-Y'-\overset{\overset{Y}{\|}}{C}-CH_2-M-R-Z^2 \quad (VII)$$

wherein:
2 M, R, Y, Y' and the same as above; and
at least one of Z' and $Z^2$ is OH, under conditions sufficient to cause attachment of said polymer to said biologically-active moiety via an ester linkage.

21. The method of claim 20, wherein Z' is CH$_3$.

22. The method of claim 20, wherein X is O.

23. The method of claim 20, wherein Q is CH$_2$—C(O)—N(H).

24. The method of claim 20, wherein Y and Y' are O.

25. The method of claim 20, wherein said polyalkylene oxide comprises polyalkylene glycol.

26. The method of claim 20, wherein said polyalkylene oxide has a molecular weight of from about 20,000 to about 80,000.

27. The method of claim 26, wherein said polyalkylene oxide has a molecular weight of from about 25,000 to about 45,000.

28. The method of claim 27, wherein said polyalkylene oxide has a molecular weight of from about 30,000 to about 43,000.

29. The method of claim 20, wherein D is selected from the group consisting of taxol, taxane or taxotere and $Y^1$ is attached to the 2' position of said D.

30. The method of claim 20, wherein D is selected from the group consisting of camptothecin, etoposide, B and podophyllotoxin.

31. The method of claim 20, wherein said polymer of formula (VII) is selected from the group consisting of:
PEG—X—CH$_2$—COOH;

HOOC—CH₂—X—PEG—X—CH₂—COOH;

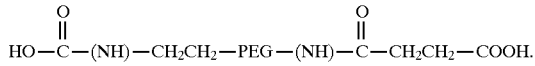

and

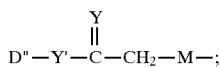

32. A method of effecting treatment in mammals with prodrugs comprising a biologically-active moiety, comprising:
administering to a mammal in need of such treatment an effective amount of a prodrug composition of claim 1.

33. A composition comprising the formula:

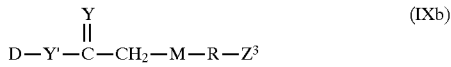 (IXb)

wherein:
D is a residue of a biologically active moiety having undergone an esterification reaction;
M is X or Q;
X is an electron withdrawing group;
Q is a moiety containing a free electron pair positioned five or six atoms from Y';
Y and Y' are independently O or S;
R is a substantially non-antigenic polymer; and
$Z^3$ is

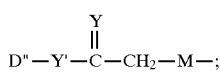

wherein D" is selected from the group consisting of dialkyl ureas, $OC_{1-4}$ alkyl moieties or carboxylic acids.

34. The composition of claim 33, wherein D is a camptothecin analog.

35. The composition of claim 33, wherein D is a taxane analog.

36. A method of preparing a composition of the formula:

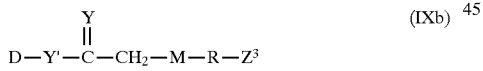 (IXb)

wherein:
D is a biologically active moiety;
M is X or Q;
X is an electron withdrawing group;
Q is a moiety containing a free electron pair positioned five or six atoms from Y';
Y and Y' are independently O or S;
R is a polyalkylene oxide; and
$Z^3$ is

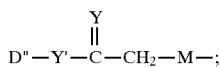

wherein D" is selected from the group consisting of dialkyl ureas, $C_{1-4}$ alkyl moieties or carboxylic acids, comprising:
reacting a biologically active moiety, D, with a polymer of the formula:

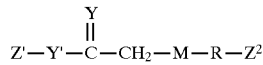 (VII)

wherein:
M, R, Y, Y' and the same as above; and
Z' and $Z^2$ are OH,
under conditions sufficient to cause attachment of said polymer to said biologically-active moiety via an ester linkage which displaces one of Z' and $Z^2$ and converts the other Z moiety to $Z^3$.

37. A method of effecting treatment in mammals with prodrugs comprising a biologically-active moiety, comprising:
administering to a mammal in need of such treatment an effective amount of a prodrug composition of claim 33.

38. The composition of claim 1, wherein said substantially non-antigenic polymer is polyalkylene oxide.

39. The composition of claim 33, wherein said substantially non-antigenic polymer is polyalkylene oxide.

40. A composition comprising the formula:

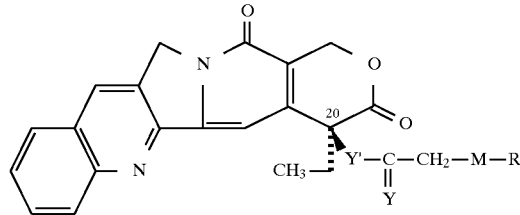

wherein:
M is X or Q;
X is an electron withdrawing group;
Q is a moiety containing a free electron pair positioned five or six atoms from Y';
Y and Y' are independently O or S;
R is a substantially non-antigenic polymer.

41. The composition of claim 40, wherein R further comprises a capping group Z.

42. The composition of claim 41, wherein Z is

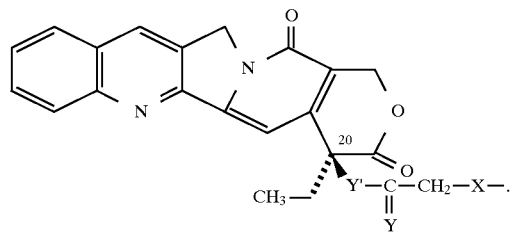

43. The composition of claim 41, wherein Z is

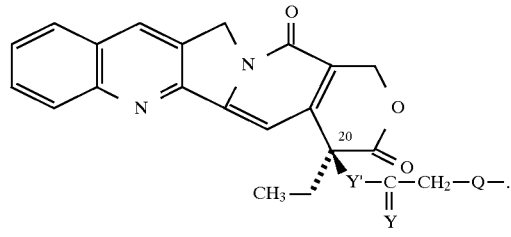

44. The composition of claim 41, having the formula:

25                                                                                       26
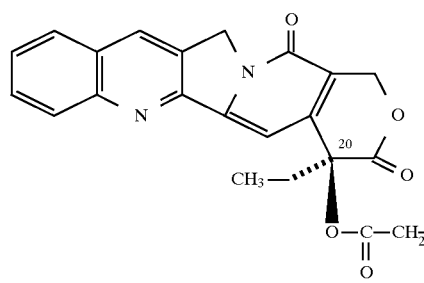 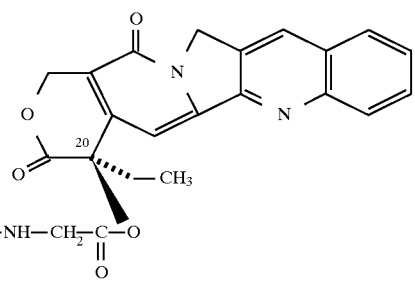
where the PEG portion thereof has a molecular weight of from about 20,000 to about 80,000.
* * * * *

UNITED STATES PATENT AND TRADEMARK OFFICE
CERTIFICATE OF CORRECTION

PATENT NO. : 5,880,131  
DATED : March 9, 1999  
INVENTOR(S) : Greenwald, Richard B. et al.

Page 1 of 1

It is certified that error appears in the above-identified patent and that said Letters Patent is hereby corrected as shown below:

ABSTRACT,
Line 13, delete "all", insert -- alkyl --.

Column 4,
Line 55, after "C", delete "(0)", insert -- (O) --.

Claim 4,
Line 3, delete "S0$_2$", insert -- SO$_2$ --.

Claim 20,
Line 17, delete "2".

Claim 30,
Line 2, delete ", B".

Signed and Sealed this

Nineteenth Day of February, 2002

JAMES E. ROGAN
Director of the United States Patent and Trademark Office

Attest:

Attesting Officer